US011103239B2

(12) United States Patent
Isch

(10) Patent No.: US 11,103,239 B2
(45) Date of Patent: Aug. 31, 2021

(54) RATCHET STAPLE

(71) Applicant: Biomet Manufacturing, LLC, Warsaw, IN (US)

(72) Inventor: Bryce A. Isch, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 546 days.

(21) Appl. No.: 15/948,196

(22) Filed: Apr. 9, 2018

(65) Prior Publication Data

US 2018/0303479 A1    Oct. 25, 2018

Related U.S. Application Data

(60) Provisional application No. 62/488,279, filed on Apr. 21, 2017.

(51) Int. Cl.
*A61B 17/06*     (2006.01)
*A61B 17/064*    (2006.01)

(52) U.S. Cl.
CPC ...... *A61B 17/0642* (2013.01); *A61B 17/0644* (2013.01); *A61B 2017/0645* (2013.01)

(58) Field of Classification Search
CPC .............. A61B 17/0642; A61B 17/064; A61B 17/0644; A61B 17/0645
See application file for complete search history.

(56) References Cited

U.S. PATENT DOCUMENTS

| | | | | |
|---|---|---|---|---|
| 3,385,299 A * | 5/1968 | Le Roy | .......... | A61B 17/08 606/218 |
| 3,709,219 A * | 1/1973 | Halloran | .......... | A61B 17/60 606/105 |
| 3,807,394 A * | 4/1974 | Attenborough | .......... | A61B 17/68 606/60 |
| 3,862,631 A * | 1/1975 | Austin | .......... | A61B 17/0642 606/60 |
| 4,852,558 A * | 8/1989 | Outerbridge | .......... | A61B 17/8009 606/75 |
| 5,246,443 A * | 9/1993 | Mai | .......... | A61B 17/0644 606/78 |
| 6,051,007 A * | 4/2000 | Hogendijk | .......... | A61B 17/08 606/151 |
| 6,336,928 B1 * | 1/2002 | Guerin | .......... | A61B 17/7059 606/282 |
| 7,635,364 B2 * | 12/2009 | Barrall | .......... | A61B 17/7059 606/70 |
| 8,382,761 B2 * | 2/2013 | Holsten | .......... | A61B 17/0644 606/75 |
| 8,936,628 B2 * | 1/2015 | Anderson | .......... | A61B 17/0401 606/216 |
| 9,675,395 B2 * | 6/2017 | Averous | .......... | A61B 17/846 |
| 10,105,170 B2 * | 10/2018 | Llas Vargas | .......... | A61B 17/68 |
| 2002/0103489 A1 * | 8/2002 | Ku | .......... | A61B 17/0642 606/75 |
| 2005/0251155 A1 * | 11/2005 | Orban | .......... | A61B 17/115 606/153 |
| 2008/0172088 A1 * | 7/2008 | Smith | .......... | A61B 17/0644 606/219 |

* cited by examiner

*Primary Examiner* — Julie A Szpira

(74) *Attorney, Agent, or Firm* — Schwegman Lundberg & Woessner, P.A.

(57) ABSTRACT

An apparatus including a first leg; a second leg distant from the first leg; and a bridge extending between and connecting the first leg to the second leg; wherein the bridge is configured such that a length of the bridge between the first leg and the second leg can be incrementally adjusted.

9 Claims, 4 Drawing Sheets

RATCHET STAPLE

CLAIM OF PRIORITY

This application claims the benefit of U.S. Provisional Patent Application Ser. No. 62/488,279, filed on Apr. 21, 2017, the benefit of priority of which is claimed hereby, and which is incorporated by reference herein in its entirety.

FIELD

The present subject matter relates to an apparatus for use in surgery and more specifically to a medical staple.

BACKGROUND

It is common to create fixation across an osteotomy or fusion site. For example, by surgeons performing fusions or osteotomies in a foot. Different fixation staples have various sizes to allow a surgeon to choose from the sizes depending on need. However, the gaps between the sizes do not allow for the precise adjustment a surgeon would desire to have. Thus, when surgeons utilize such devices they are limited by the amount of sizing options available to them.

OVERVIEW

In a first example, an apparatus includes a first leg; a second leg distant from the first leg; and a bridge extending between and connecting the first leg to the second leg; wherein the bridge is configured such that a length of the bridge between the first leg and the second leg can be incrementally adjusted.

In Example 2, the apparatus of Example 1 can include a male bridge portion including a plurality of teeth and a female bridge portion having at least one projection to engage the plurality of teeth.

In Example 3, the apparatus of Example 2 can include the male bridge portion including a slot extending longitudinally through the male bridge portion.

In Example 4, the apparatus of Example 2 can include the male bridge portion including the plurality of teeth on both sides of the male bridge portion.

In Example 5, the apparatus of Example 2 can include the male bridge portion including a plurality of teeth on one side of the male bridge portion.

In Example 6, the apparatus of Example 1 can include a female bridge portion including a plurality of teeth and a male bridge portion having at least one projection to engage the plurality of teeth.

In Example 7, the apparatus of Example 1 can include at least a portion of the first leg, the second leg, and the bridge being formed of a porous metal.

In Example 8, the apparatus of Example 1 can include the first leg and the second leg being positioned such that the first leg and the second leg are angled away from each other.

In Example 9, the apparatus of Example 1 can include the bridge including a wedge profile where a top of the bridge is wider that a bottom of the bridge.

In Example 10, a system includes a plurality of fixation devices having a plurality of different sizes, wherein each of the plurality of fixation devices includes: a first leg; a second leg distant from the first leg; and a bridge extending between and connecting the first leg to the second leg; wherein the bridge is configured such that a length of the bridge between the first leg and the second leg can be incrementally adjusted.

In Example 11, the system of Example 10 can include the bridge having a male bridge portion including a plurality of teeth and a female bridge portion having at least one projection to engage the plurality of teeth.

In Example 12, the system of Example 11 can include the male bridge portion having a slot extending longitudinally through the male bridge portion.

In Example 13, the system of Example 11 can include the male bridge portion having the plurality of teeth on both sides of the male bridge portion.

In Example 14, the system of Example 13 can include the bridge having a female bridge portion including a plurality of teeth and a male bridge portion having at least one projection to engage the plurality of teeth.

In Example 15, the system of Example 14 can include at least a portion of the first leg, the second leg, and the bridge being formed of a porous metal.

In Example 16, a method includes positioning a fixation device within a bone, the fixation device including a first leg, a second leg distant from the first leg, and a bridge extending between and connecting the first leg to the second leg; and incrementally adjusting a length of the bridge between the first leg and the second leg.

In Example 17, the method of Example 16 can include the bridge having a male bridge portion including a plurality of teeth and a female bridge portion having at least one projection to engage the plurality of teeth.

In Example 18, the method of Example 17 can include the male bridge portion having a slot extending longitudinally through the male bridge portion.

In Example 19, the method of Example 16 can include the bridge having a female bridge portion including a plurality of teeth and a male bridge portion having at least one projection to engage the plurality of teeth.

In Example 20, the method of Example 16 can include at least a portion of the first leg, the second leg, and the bridge being formed of a porous metal.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
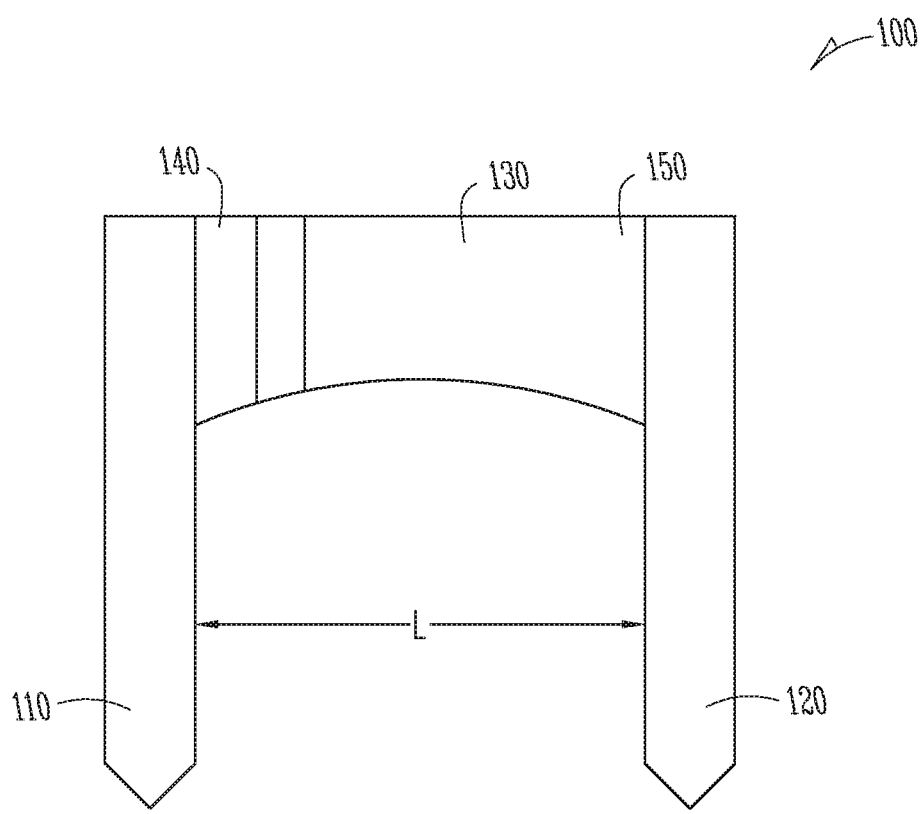
FIG. 1 shows a front view of a fixation device in accordance with one embodiment.

FIG. 1 shows a front view of a fixation device 100 in accordance with one embodiment. Fixation device 100 can be an implant such as a staple, which can be used for surgeons performing fusions or osteotomies in the foot, for example.

Fixation device 100 generally includes a first leg 110, a second leg 120, and a bridge 130. The bridge 130 can extend between and connect the first leg 110 to the second leg 120, which are positioned a certain distance apart from each other. First leg 110 and second leg 120 extend downward in generally similar directions. Thus, from a side view (perpendicular to FIG. 1) the first leg 110 and second leg 120 lie in the same plane. In one example, from a front perspective, the first leg 110 and the second leg 120 can be positioned relative to each other such that the first leg and the second leg are angled away from each other so as to compress the joint or fracture line as the device 100 is inserted.

Fixation device 100 can be formed from a solid substrate or can be formed so that at least a portion of the first leg 110, the second leg 120, and the bridge 130 are formed of a porous metal. For example, the fixation device 100 can include a solid core and can be manufactured via additive manufacturing.

In one example, the fixation device 110 is configured such that a length L of the bridge 130 can be incrementally adjusted between the first leg 110 and the second leg 120.

Figure 2:
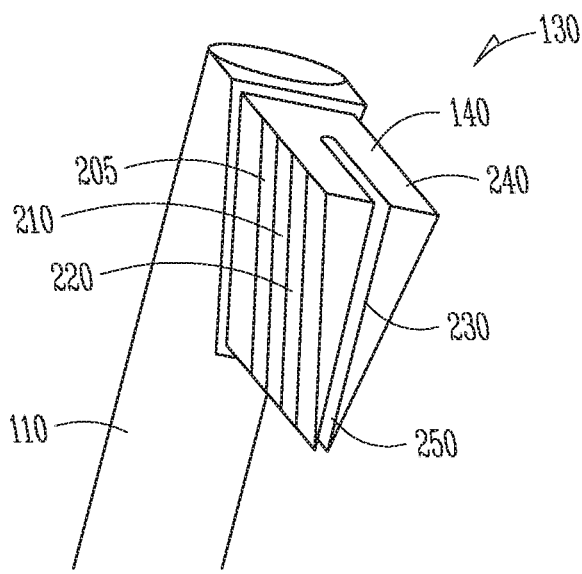
FIG. 2 shows a perspective view of a first portion of the fixation device, in accordance with one embodiment.
Figure 3:
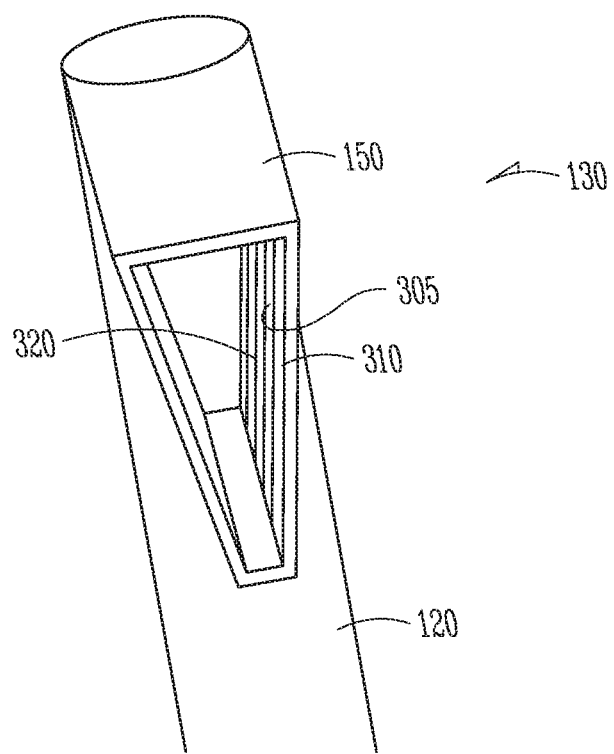
FIG. 3 shows a perspective view of a second portion of the fixation device, in accordance with one embodiment.

Referring now also to FIGS. 2 and 3, these Figures show perspective views of a first, male bridge portion 140 of the fixation device 100, and a second, female bridge portion 150 of the fixation device, in accordance with one embodiment.

The male bridge portion 140 and female bridge portion 150 are shaped so that the male bridge portion 140 is received within the female bridge portion 150, and the two portion 140 and 150 can be incrementally moved toward each other.

The male bridge portion 140 extends from the first leg 110 and includes at least one projection 205, such as one or a plurality of teeth 210 on an outer surface 220 of the male bridge portion 140. In one example, the male bridge portion 140 can include the plurality of teeth 210 on both side surfaces of the male bridge portion 140. In another example, the male bridge portion 140 includes a plurality of teeth 210 on one side of the male bridge portion 140.

Likewise, the female bridge portion 150 extends from the second leg 120 and includes at least one projection 305, such as one or a plurality of teeth 310 on at least one inner surface 320 of the female bridge portion 150.

The projections 205, 305 or teeth 210, 310 of the bridge portions 140, 150 thus provide a ratchet mechanism to allow the bridge portions 140, 150 to be gradually and incrementally advanced toward each other. The teeth can progressively engage the projection upon advancement of the male and the female portions 140, 150 toward each other.

In one example, such a ratchet style mechanism can include a concept similar to that of a commonly used nylon zip tie, which utilize a male tooth pattern which engages with a female pocket limiting the separation of components.

The inclusion of the ratchet mechanism for the fixation device 100 provides a surgeon the ability to incrementally adjust the amount of compression applied, as well as better fit the anatomic requirements of their patients. Thus, multiple compression loads can be applied using a single size implant. In past devices, a given family of such fixation devices could come in a range of sizes such as 15 mm, 20 mm, and 25 mm, for example. Such a gap between the sizes of the devices does not allow for incremental adjustment by the surgeon across the fixation site. As anatomies vary by gender, race, age, etc., the need to provide incremental or infinite amounts of adjustment within the implant design exists.

In one example, the male bridge portion 140 can include a slot 230 extending longitudinally through the male bridge portion 140 and extending from a top 240 to a bottom 250 of the male bridge portion 140. Slot 230 provides some give to allow the sides of the male bridge portion to squeeze together and allow the teeth 220 of the male bridge portion 140 to deform within the pockets of the female projection(s) included on the mating, female bridge portion 150.

In one example, the bridge 130 can include a wedge profile where the top 240 of the bridge 130 is wider that the bottom 250 of the bridge 130 such that the side surfaces are tapered. Thus, when the bridge 140 is fully inserted into the bone, the bridge can mitigate shear and torsion micromotion along the joint or fracture line.

Figure 4:
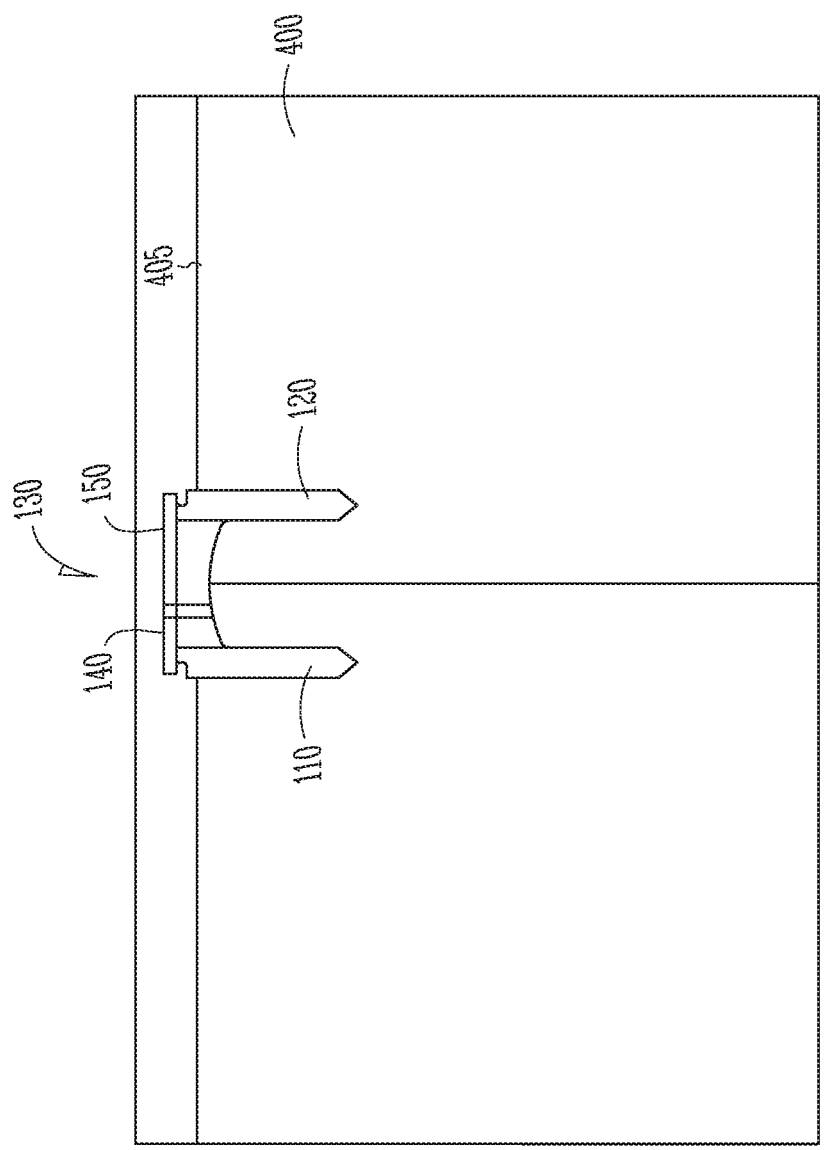
FIG. 4 shows a schematic representation of the fixation device being inserted into a bone.

FIG. 4 shows a schematic representation of the fixation device 100 being inserted into a bone 400.

In an example use, a surgeon implants the fixation device 100 into the bone 400 with similar preparation as to existing devices. Either before insertion or when the fixation device 100 is a certain distance within the bone 400 the surgeon can incrementally adjust the length of the bridge 130 between the first leg 110 and the second leg 120 of the fixation device 100 by application of compression by the surgeon to "lock" the ratchet teeth at the desired location. The fixation device can then be further inserted so that a top surface of the fixation device 100 is flush with a top surface 405 of the bone 400.

Figure 5:
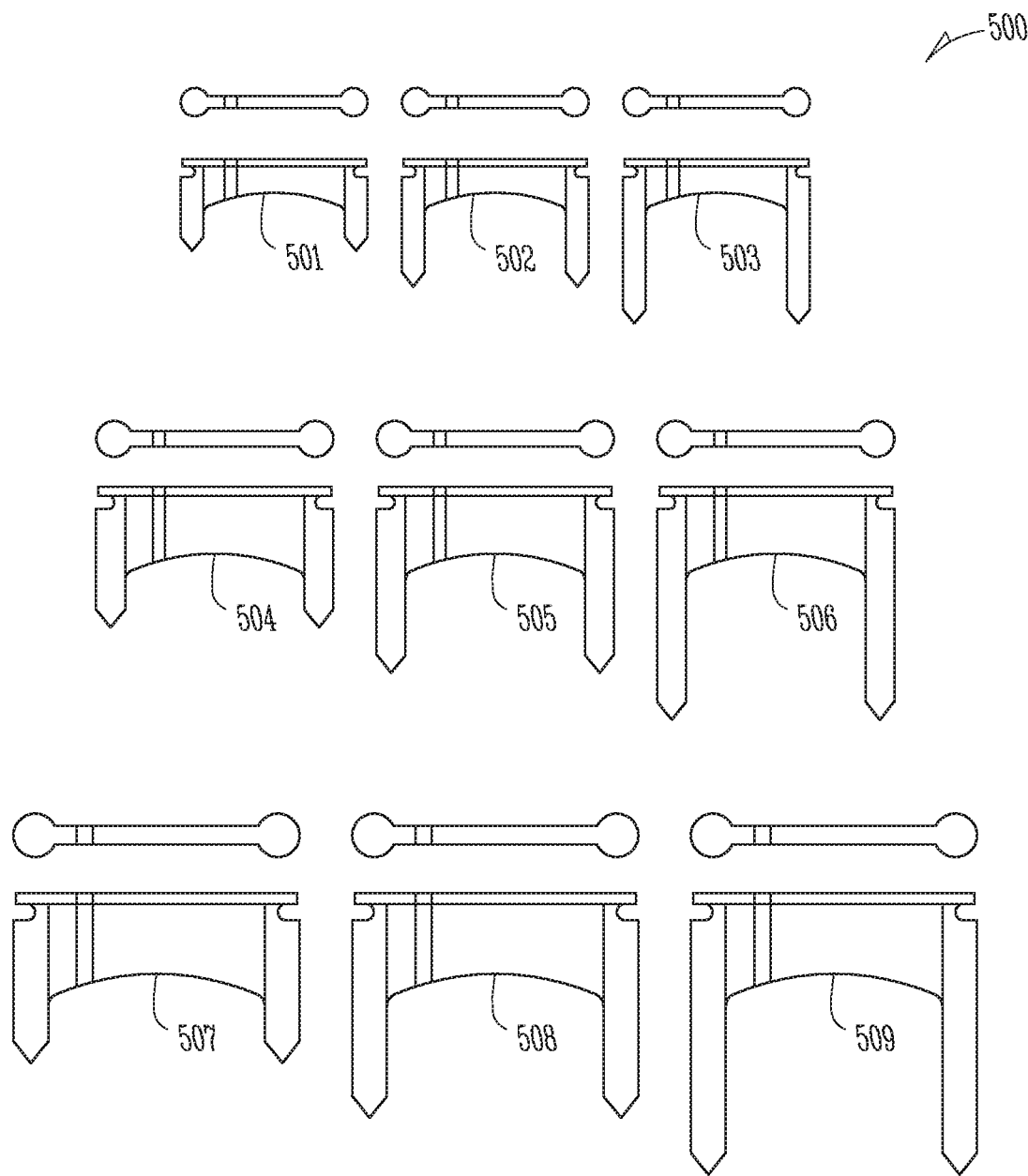
FIG. 5 shows a plurality of different size fixation devices, in accordance with one embodiment.

FIG. 5 shows a plurality of different size fixation devices. Here a system provides a family 500 of devices to be used by a surgeon. The family can include two or more fixation devices 501-509. Each of the fixation devices 501-509 can be incrementally adjusted as discussed above. This allows a surgeon a wide variety of possible options.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising:
 a first leg;
 a second leg distant from the first leg; and
 a bridge extending between and connecting the first leg to the second leg;
 wherein the bridge is configured such that a length of the bridge between the first leg and the second leg can be incrementally adjusted;
 wherein bridge includes a male bridge portion including a plurality of teeth and a female bridge portion having at least one projection to engage the plurality of teeth; and
 wherein the male bridge portion includes a slot extending longitudinally through the male bridge portion and extending all the way through the male bridge portion from a top surface of the male bridge portion to a bottom surface of the male bridge portion and configured to allow side portions of the male bridge portion to be squeezed together.

2. The apparatus of claim 1, wherein the male bridge portion includes the plurality of teeth on both sides of the male bridge portion.

3. The apparatus of claim 1, wherein the male bridge portion includes a plurality of teeth on one side of the male bridge portion.

4. The apparatus of claim 1, wherein at least a portion of the first leg, the second leg, and the bridge are formed of a porous metal.

5. The apparatus of claim 1, wherein the first leg and the second leg are positioned such that the first leg and the second leg are angled away from each other.

6. The apparatus of claim 1, wherein the bridge includes a wedge profile where a top of the bridge is wider that a bottom of the bridge.

7. A system comprising:
 a plurality of fixation devices having a plurality of different sizes, wherein each of the plurality of fixation devices includes:
 a first leg;
 a second leg distant from the first leg; and
 a bridge extending between and connecting the first leg to the second leg;
 wherein the bridge is configured such that a length of the bridge between the first leg and the second leg can be incrementally adjusted;
 wherein bridge includes a male bridge portion including a plurality of teeth and a female bridge portion having at least one projection to engage the plurality of teeth; and
 wherein the male bridge portion includes a slot extending longitudinally through the male bridge portion and extending all the way through the male bridge portion from a top surface of the male bridge portion to a bottom surface of the male bridge portion and configured to allow side portions of the male bridge portion to be squeezed together.

8. The system of claim 7, wherein the male bridge portion includes the plurality of teeth on both sides of the male bridge portion.

9. The system of claim 7, wherein at least a portion of the first leg, the second leg, and the bridge are formed of a porous metal.

* * * * *